(12) United States Patent
Lin et al.

(10) Patent No.: US 6,808,512 B1
(45) Date of Patent: Oct. 26, 2004

(54) SAFETY SYRINGE

(76) Inventors: Hsiu-Chih Lin, No. 1, Tatung Rd., Pentang Village, Wufeng Hsiang, Taichung Hsien, Taiwan, R.O.C. (TW); Jih-Hsiung Yang, No. 822, Chungcheng Rd., Wufeng Hsiang, Taichung Hsien, Taiwan, R.O.C. (TW)

( * ) Notice: Subject to any disclaimer, the term of this patent is extended or adjusted under 35 U.S.C. 154(b) by 0 days.

(21) Appl. No.: 10/409,054

(22) Filed: Apr. 9, 2003

(51) Int. Cl.$^7$ ................................................ A61M 5/32
(52) U.S. Cl. .................... 604/196; 604/220; 604/231
(58) Field of Search .............................. 604/82, 93.01, 604/181–183, 186–188, 191–192, 194–195, 197–198, 207, 218, 214–215, 220–221, 231, 240, 243, 263, 264, 272, 110; 128/919

(56) References Cited

U.S. PATENT DOCUMENTS 4,941,883 A * 7/1990 Venturini .................... 604/186
6,162,197 A * 12/2000 Mohammad ................ 604/195
6,468,250 B2 * 10/2002 Yang ........................... 604/198

* cited by examiner

Primary Examiner—Brian L. Casler
Assistant Examiner—Michael M Thompson
(74) Attorney, Agent, or Firm—Rosenberg, Klein & Lee

(57) ABSTRACT

A safety syringe has a hollow barrel, a plunger, a tube, a needle hub, a spring and a plug. The hollow barrel has an outside surface, a proximal open end and a distal closed end. The plunger is mounted slidably inside the hollow barrel. The tube has a proximal open end and a distal open end and is attached longitudinally to the outside surface of the hollow barrel. The needle hub and the spring are mounted inside the tube, and the needle can extend out of the distal open end of the tube. A first through hole defined in the hollow barrel and a second through hole is defined in the tube align with each other. The needle is extended out from the distal end of the tube to take a blood sample. The used needle is retracted into the tube after use to keep people from getting injured or infected.

4 Claims, 4 Drawing Sheets

SAFETY SYRINGE

BACKGROUND OF THE INVENTION

1. Field of the Invention

The present invention relates to a syringe, and more particularly to a safety syringe that can safely hold a used needle and prevent the syringe from being used more than once.

2. Description of Related Art

A conventional syringe has a hollow barrel, a plunger and a needle hub. The needle hubs of conventional syringes are easily inclined during use so the needle hubs are difficult to retract into the barrel. Due to contagious diseases, the needles of syringes and even the hollow barrels and plungers, should not be used again and should be discarded immediately after use. Also, to keep nurses, doctors or workers who deal with discarded syringes from getting injured or infected by used needles, a safety syringe is needed. The conventional safety syringe often has a complex structure, so to provide a simple and effective safe design for the needles of syringes is still needed.

To overcome the shortcomings of conventional syringes, the present invention provides a safety syringe to mitigate or obviate the aforementioned problem.

SUMMARY OF THE INVENTION

The primary objective of the present invention is to provide a safety syringe that has a simpler structure than the conventional safety syringe and improves safety. The safety syringe in accordance with the present invention comprises a hollow barrel, a plunger, a tube and a needle hub.

The hollow barrel has a proximal open end, a distal closed end, an outside surface, a dovetail keyway and a first through hole. The plunger is slidably mounted inside the hollow barrel. The tube has a proximal open end and a distal open end and is mounted on the hollow barrel. The needle hub and the spring are mounted inside the tube, and the needle selectively extends from the proximal open end of the tube. The first through hole is defined in the hollow barrel through the dovetail keyway, and a second through hole is defined in the tube. The first through hole faces the second through hole.

When using the safety syringe, the needle hub extends out of the tube to draw a blood sample. When finishing taking a blood sample, the used needle hub is retracted inside the tube to keep the used needle from injuring or infecting a person.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
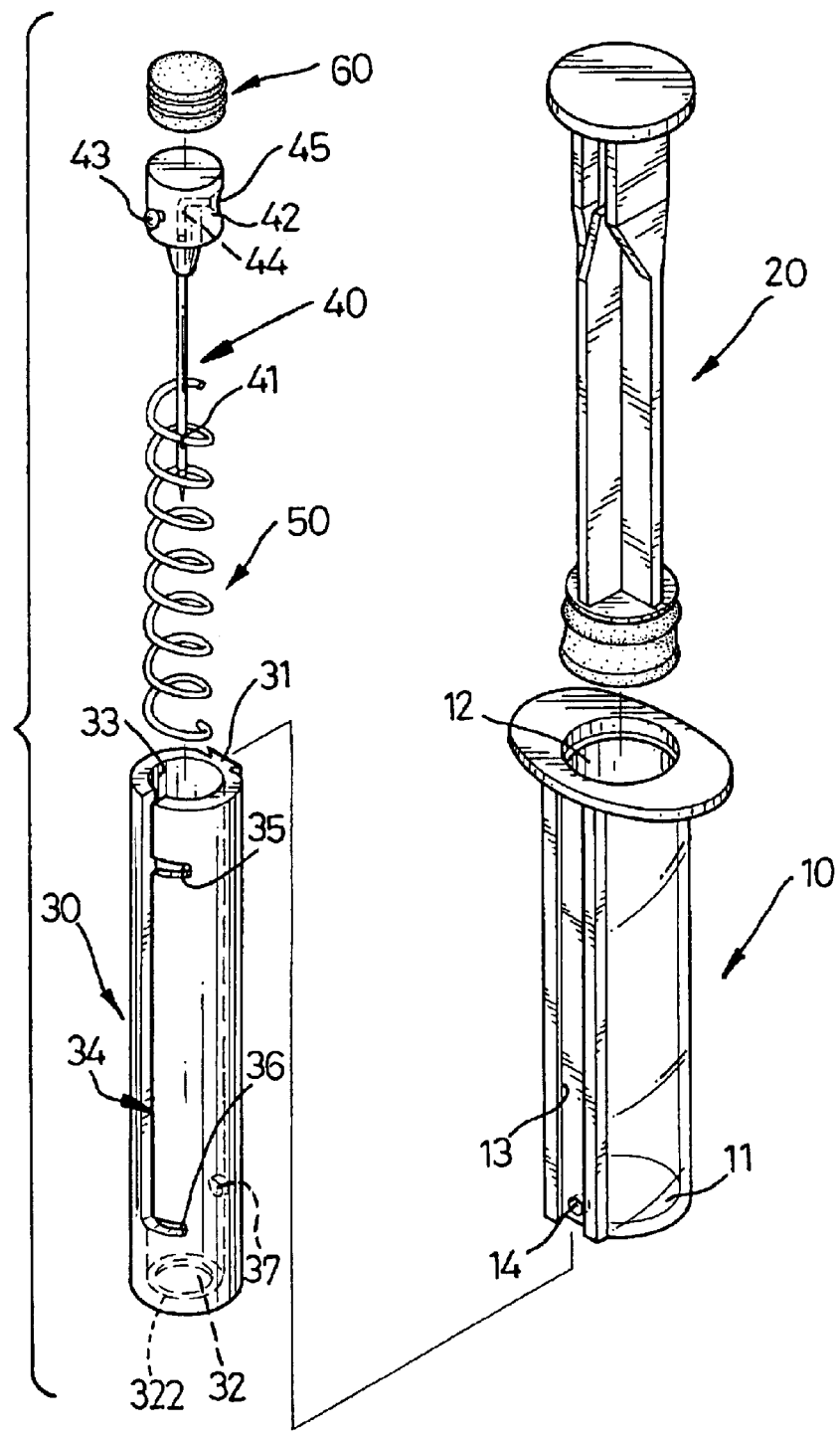
FIG. 1 is an exploded perspective view of a safety syringe in accordance with the present invention.
Figure 2:
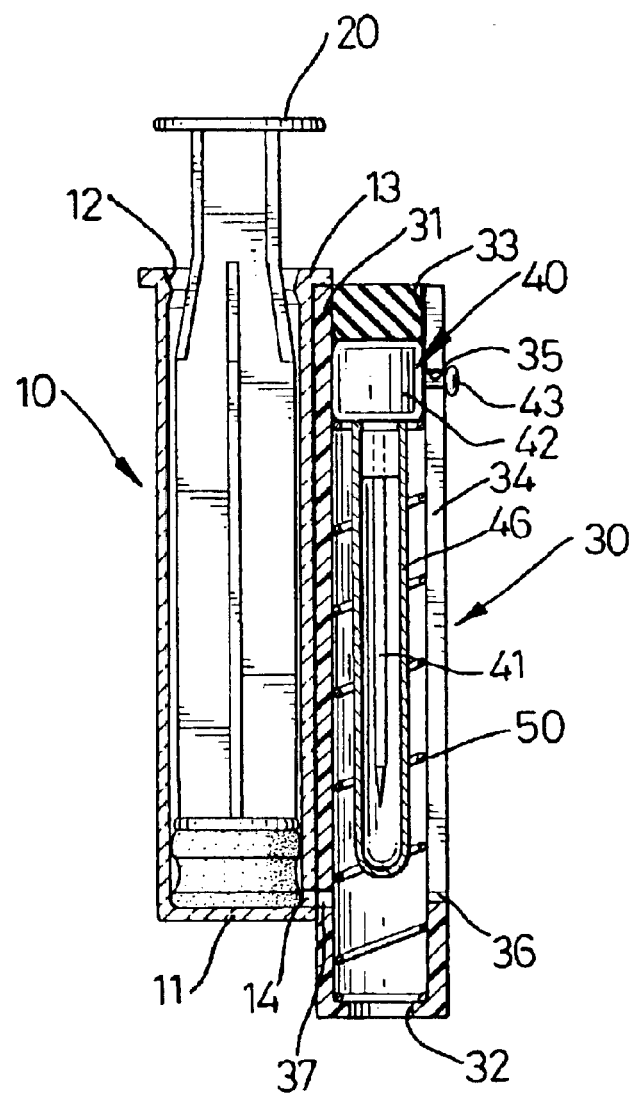
FIG. 2 is a side plan view in partial section of the safety syringe in FIG. 1 with the plunger pressed into the hollow barrel and a covered needle in the tube.

With reference to FIGS. 1 and 2, a safe syringe in accordance with the present invention has a hollow barrel (10), a plunger (20), a tube (30) and a needle hub (40).

The hollow barrel (10) is cylindrical and has a distal closed end (11), a proximal open end (12), a sidewall (not numbered), an outside surface (not numbered), an annular flange (not numbered), a dovetail keyway (13) and a first through hole (14). The annular flange is defined radially around and extends out from the proximal open end (12). The dovetail keyway (13) is formed longitudinally on the outside surface of the hollow barrel (10). The first through hole (14) is defined through the sidewall in the dovetail keyway (13) near the distal closed end (11).

The plunger (20) has a proximal end (not numbered), a distal end (not numbered) and a seal (not numbered) and is slidably mounted inside the hollow barrel (10). The seal is attached to the distal end of the plunger (20).

The tube (30) is connected to the hollow barrel (10) and has an outside surface (not numbered), a dovetail key (31), a lip (322), a distal open end (32), a proximal open end (33), a guide slot (34), a sidewall (not numbered) and a second through hole (37). The dovetail key (31) is formed longitudinally on and extends from the outside surface and engages the dovetail keyway (13) on the hollow barrel (10). The lip (322) is formed at the distal open end (32) and protrudes radially inward so that the distal open end (32) is smaller than the proximal open end (33). The guide slot (34) has a proximal end (not numbered), a distal end (not numbered), a retracted locking slot (35) and an extended locking slot (36) and is defined longitudinally through the sidewall of the tube (30) diametrically opposite from the dovetail key (31). The proximal end of the guide slot (34) can be open and is at the proximal open end (33) of the tube (30). The retracted locking slot (35) is formed near the proximal end of and perpendicular to the guide slot (34). The extending locking slot (36) is formed at the distal end of and perpendicular to the guide slot (34). The second through hole (37) is defined through the sidewall of the tube (30) and the dovetail key (31) and faces and aligns with the first through hole (14) defined through the hollow barrel (10). The tube (30) also can connect to the hollow barrel (10) in other ways such as by being integrally formed together with the hollow barrel (10).

The safety syringe in accordance with the present invention further comprises a spring (50) and a plug (60). The spring (50) has a distal end (not numbered) and a proximal end (not numbered) and is inserted mounted into the tube (30). The distal end of the spring (50) abuts the lip in the distal open end (32) of the tube (30).

The needle hub (40) is slidably mounted inside the tube (30) and has a needle (41), a stopper (42), a guide stub (43), a fluid channel (44) and a tapered hole (45). The stopper (42) is cylindrical and has a top surface (not numbered), a bottom surface (not numbered) and a cylindrical surface (not numbered). The bottom surface abuts the distal open end (32). The needle (41) has a longitudinal fluid passage (not shown), and can pass through the spring (50) and is mounted in the bottom surface of the stopper (42). The fluid channel (44) has a first end (not numbered) and a second end (not numbered). The first end is defined through the bottom surface of the stopper (42), and the second end is defined through the cylindrical surface of the stopper (42). The first end of the fluid channel (44) is connected to the needle (41), and the second end of the fluid channel (44) is connecting to the tapered hole (45) that is formed in the cylindrical surface. The guide stub (43) is attached to the cylindrical surface of the stopper (42) so the tapered hole (45) aligns with the second through hole (37) when the guide stub (43) is fully seated in the extended locking slot (36).

With further reference to FIG. 2, the needle hub (40) may optionally include a needle cap (46). The needle cap (46) is detachably attached to the bottom surface of the stopper (42) to cover the needle (41) to protect the needle (41) from contaminants and to keep the needle (41) from injuring a person when the needle (41) is being extended from the tube (30). The needle cap (46) is removed from the needle (41) and discarded to draw a blood sample or medicine into the hollow barrel (10).

The plug (60) is cylindrical and is mounted securely inside the distal open end (33) of the tube (30) to hold the needle hub (40) inside the tube (30).

Figure 3:
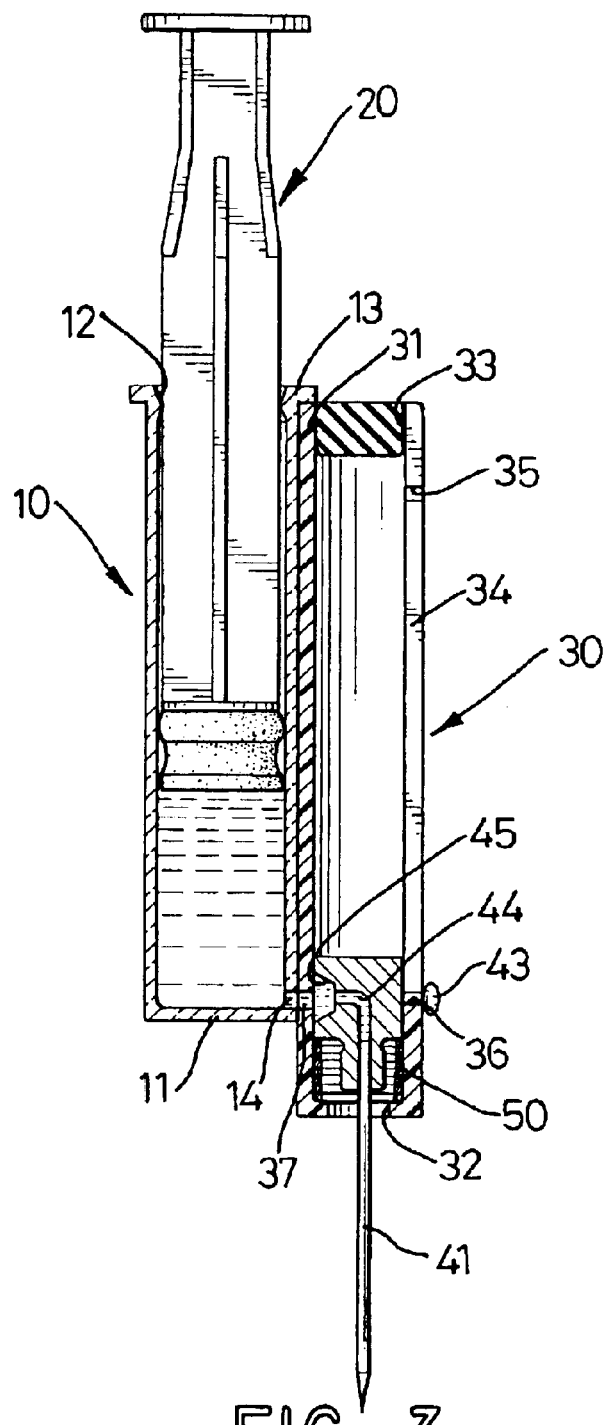
FIG. 3 is an operational side plan view in partial section of the safety syringe in FIG. 1 with the plunger partially retracted from the hollow barrel and the needle extending from the tube.

With reference to FIGS. 2 and 3, when taking blood or putting medicine into a patient's body, the user moves the stopper (42) from the retracted locking slot (35) to the guide slot (34) by means of holding the guide stub (43). The stopper (42) is slid toward the distal end of the guide slot (34) and is moved into the extended locking slot (36) to hold the needle (41) outside the distal open end (32) of the tube (30) and to align the tapered hole (45) with the second through hole (37) in the tube (30). The spring (50) is compressed between the lip (322) at the proximal open end (32) and the bottom surface of the needle hub (40). The plunger (20) is pulled toward the proximal end of the hollow barrel (10) so that a blood sample or medicine can be drawn through the needle (41), the fluid channel (44), the second through hole (37) and the first through hole (14) into the hollow barrel (10).

Figure 4:
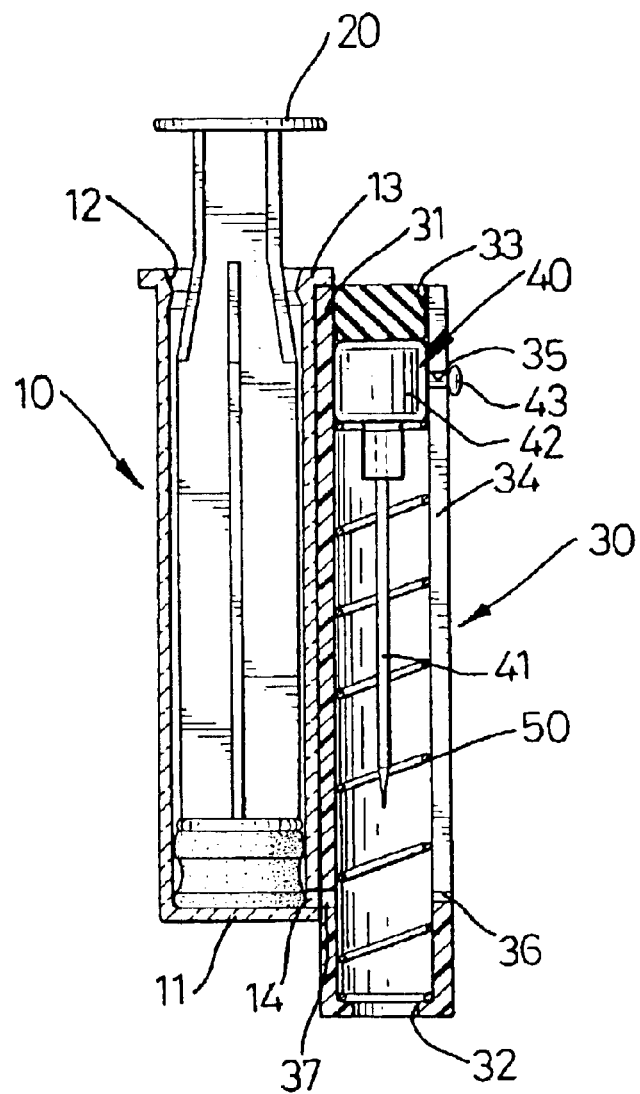
FIG. 4 is an operational side plan view in partial section of the safety syringe in FIG. 1 with the plunger pressed into the barrel and a used needle retracted into the tube.

With reference to FIGS. 3 and 4, used syringes should be discarded after use. The guide stub (43) is released from the extended locking slot (36), and the spring (50) pushes the guide stub (43) toward the proximal end of the guide slot (34). The spring (50) also holds the needle hub (40) and the needle (41) in the tube (30). The needle cap (46) can be inserted through the distal open end (32) of the tube (30) to cover the used needle (41) to further protect people who deal with the used syringes.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising:
    a hollow barrel having a distal closed end; a proximal open end; a sidewall; an outside surface; a first through hole defined through the sidewall; and, a dovetail keyway defined longitudinally on the outside surface, the first through hole being defined through the dovetail keyway;
    a plunger slidably mounted inside the hollow barrel;
    a tube connected to the hollow barrel being cylindrical and having a proximal open end; a distal open end; a sidewall; a lip defined inside the distal open end; a guide slot defined longitudinally through the tube from the proximal open end toward the distal open end and having a proximal end and a distal end; a retracted locking slot defined through the tube perpendicular to the guide slot and communicating with the guide slot near the proximal end of the guide slot; an extended locking slot defined through the tube perpendicular to the guide slot and communicating with the distal end of the guide slot; and a second through hole defined through the sidewall; the tube including a dovetail key engaged into the dovetail keyway; the second through hole being defined through the dovetail key aligning with the first through hole; and,
    a needle hub slidably mounted inside the tube and having a stopper having a top surface, a bottom surface and a cylindrical surface;
    a needle with a longitudinal fluid passage and mounted in the bottom surface of the stopper;
        a fluid channel defined through the stopper and having a first end defined through the bottom surface of the stopper and connected to the needle; and a second end;
        a guide stub attached to the cylindrical surface of the stopper and moveably received in the guide slot in the tube; and
        a tapered hole formed in the cylindrical surface and communicating with the second end of the fluid channel so the tapered hole aligns with the second through hole when the guide stub is fully seated in the extended locking slot.

2. The safety syringe as claimed in claim 1, wherein the hollow barrel and the tube are integrally formed together.

3. The safety syringe as claimed in claim 1 further comprising a spring inserted into the tube and the needle is inserted through the spring.

4. The safety syringe as claimed in claim 1 further comprising a plug inside the proximal open end of the tube.

* * * * *